United States Patent
Kuepper et al.

(10) Patent No.: US 11,806,646 B2
(45) Date of Patent: Nov. 7, 2023

(54) DISTILLATION METHOD WITH CONTROLLED ENERGY SUPPLY

(71) Applicant: Covestro Intellectual Property GmbH & Co. KG, Leverkusen (DE)

(72) Inventors: Achim Kuepper, Leverkusen (DE); Philipp Frenzel, Bottrop (DE); Manfred Kobylka, Burscheid (DE)

(73) Assignee: Covestro Intellectual Property GmbH & Co. KG, Leverkusen (DE)

(*) Notice: Subject to any disclaimer, the term of this patent is extended or adjusted under 35 U.S.C. 154(b) by 57 days.

(21) Appl. No.: 17/285,263

(22) PCT Filed: Oct. 21, 2019

(86) PCT No.: PCT/EP2019/078556
§ 371 (c)(1),
(2) Date: Apr. 14, 2021

(87) PCT Pub. No.: WO2020/083830
PCT Pub. Date: Apr. 30, 2020

(65) Prior Publication Data
US 2021/0370197 A1    Dec. 2, 2021

(30) Foreign Application Priority Data

Oct. 24, 2018    (EP) .................................. 18202307.7

(51) Int. Cl.
*B01D 3/42*    (2006.01)
*B01D 3/32*    (2006.01)
*B01D 3/14*    (2006.01)

(52) U.S. Cl.
CPC ............. *B01D 3/322* (2013.01); *B01D 3/148* (2013.01); *B01D 3/42* (2013.01); *B01D 3/4283* (2013.01); *B01D 2259/65* (2013.01)

(58) Field of Classification Search
None
See application file for complete search history.

(56) References Cited

U.S. PATENT DOCUMENTS

| | | | |
|---|---|---|---|
| 3,230,158 A | 1/1966 | Molique | |
| 4,024,027 A * | 5/1977 | Boyd | B01D 3/4238 203/99 |

(Continued)

FOREIGN PATENT DOCUMENTS

| | | |
|---|---|---|
| DE | 19531806 C1 | 4/1997 |
| JP | 2000302725 A | 10/2000 |

OTHER PUBLICATIONS

International Search Report, PCT/EP2019/078556, dated Dec. 6, 2019, Authorized officer: J. Van Ganswijk.

*Primary Examiner* — Jonathan Luke Pilcher
(74) *Attorney, Agent, or Firm* — John E. Mrozinski, Jr.

(57) ABSTRACT

The present invention relates to a process for thermally separating a mixture comprising a first main component and a second main component, where the boiling point of the first main component is lower than the boiling point of the second main components. The invention further relates to a system for thermal separation comprising a computer for control of the thermal separation which is set up to control the process of the invention. By means of predetermined thermodynamic models, pressure and temperature data are used to ascertain the proportions of first and second main component in bottom product streams.

14 Claims, 1 Drawing Sheet

(56) References Cited

U.S. PATENT DOCUMENTS

| | | | |
|---|---|---|---|
| 4,578,151 A | | 3/1986 | Soderstrom et al. |
| 5,047,125 A | * | 9/1991 | Meier .................. B01D 3/4238 |
| | | | 203/99 |
| 5,368,699 A | | 11/1994 | Rhiel et al. |
| 11,235,260 B2 | * | 2/2022 | Schweigert ........... C07C 17/383 |
| 2016/0048139 A1 | | 2/2016 | Samples et al. |
| 2019/0184304 A1 | * | 6/2019 | Schweigert ............ B01D 3/425 |

* cited by examiner

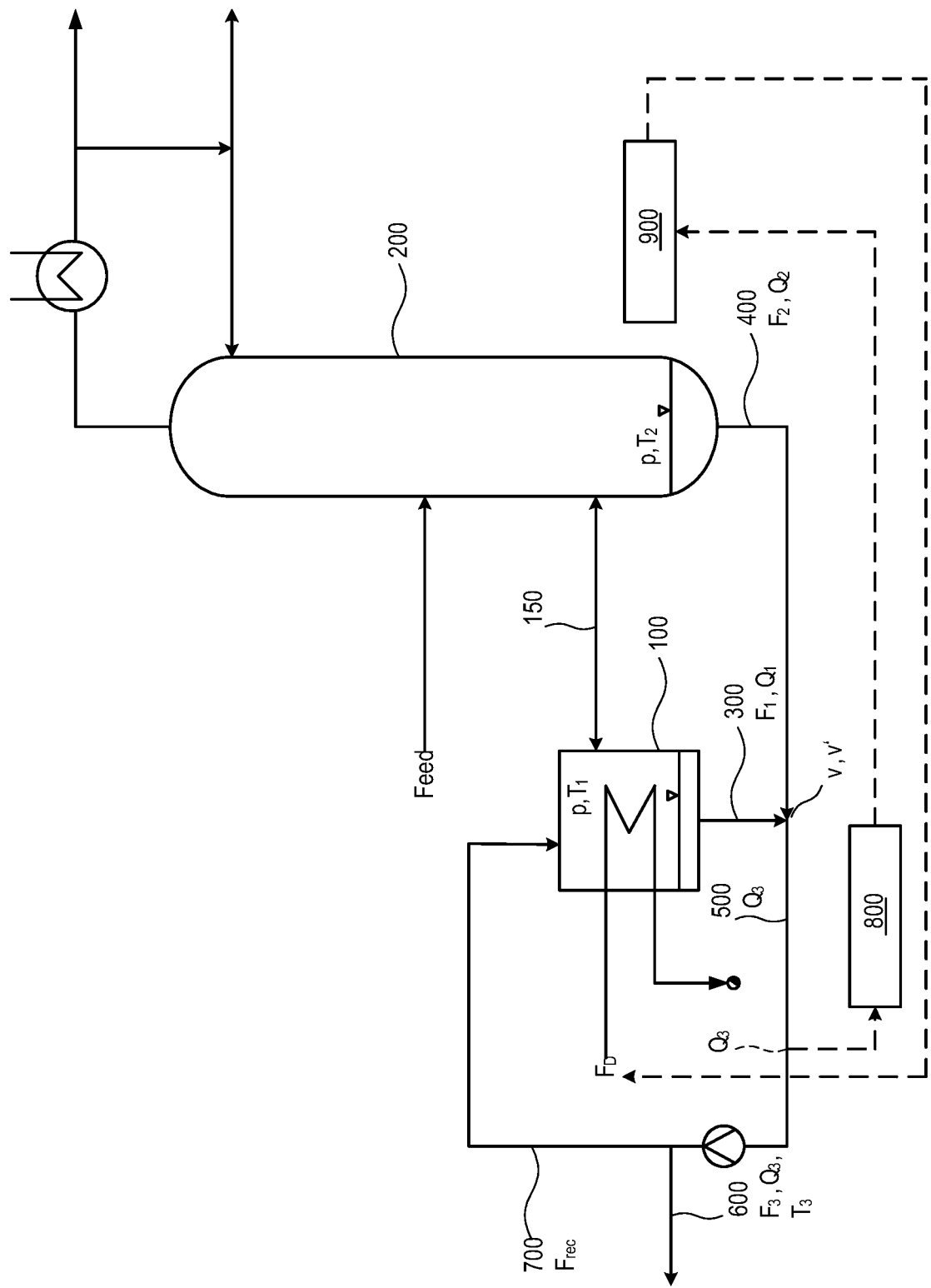

DISTILLATION METHOD WITH CONTROLLED ENERGY SUPPLY

CROSS REFERENCE TO RELATED APPLICATIONS

This application is a national stage application under 35 U.S.C. § 371 of PCT/EP2019/078556, filed Oct. 21, 2019, which claims benefit of European Application No. 18202307.7, filed Oct. 24, 2018, both of which are incorporated herein by reference in their entirety.

FIELD OF THE INVENTION

The present invention relates to a process for thermally separating a mixture comprising a first main component and a second main component, where the boiling point of the first main component is lower than the boiling point of the second main component. The invention further relates to a system for thermal separation comprising a computer for control of the thermal separation which is set up to control the process of the invention.

BACKGROUND OF THE INVENTION

Processes for real-time monitoring, estimation and assistance of decision-making in chemical plants are known, for example, in WO 2014/175962 A1. What is disclosed is a real-time process for operating a plant conducting a chemical process. The process comprises the continuous or intermittent obtaining of one or more measurements for the process. Optionally, one or more derived process variables are estimated continuously, periodically or intermittently from measured process variables and/or mathematical models. The current state of the chemical process is estimated on the basis of the process variable measurements and/or derived process variables and the current state is assessed. Probable future process states are projected into the future, and the current and/or future probable states are combined with information in a database. The information includes preferred actions for advantageous influencing of the future process state. Plant operators are provided with the information. Optionally, manual and/or automatic actions that have an advantageous effect on the future process state are conducted.

DE 19531806 C1 discloses a process for the careful distillation of fatty acids having 6 to 24 C atoms (crude fatty acid), which have been prepared by cleavage of natural fats and oils of vegetable or animal origin or by synthetic processes, by fractional evaporation of crude fatty acid and precipitation of the various vapor fractions in condensors, in which first a part of the crude fatty acid is evaporated in a pre-evaporator, the vaporized fraction is fed into a middle region of a rectification column and at least a portion of the unevaporated fraction is fed into an underlying region of the rectification column and then the top fraction of the rectification column is separated. The vaporized portion of the crude fatty acid in the vapor state is fed into the central region of the rectification column and the entire non-evaporated fraction of crude fatty acid is fed to the bottom of the rectification column, wherein the main stream is withdrawn as a side stream from the column and the side draw is below the feed of the evaporated portion of the crude fatty acid.

U.S. Pat. No. 4,578,151 discloses that the Reid Vapor Pressure of a hydrocarbon mixture consisting essentially of hydrocarbons selected from the same series is determined based on the actual temperature and vapor pressure of the hydrocarbon mixture. The thus determined Reid Vapor Pressure may be compared to a set point for the Reid Vapor Pressure with the results of the comparison being utilized to maintain the actual Reid Vapor Pressure substantially equal to the desired Reid Vapor Pressure.

An important parameter for an effective mode of operation in the HDI process for preparation of hexamethylene 1,6-diisocyanate (HDI) is the setting of the concentration of monochlorobenzene (MCB). The MCB concentration has a major influence on the HDI process. Moreover, it is advantageous to aim for a constant mode of operation of the MCB cycle, for example via interventions by the plant operator or automation, such that the MCB cycle can be optimized as part of the HDI process.

For closed-loop control (via interventions by the plant operator or automation) of the MCB cycle in the HDI process, timely detection of the MCB concentration would be desirable. Typically, for this purpose, the concentration is determined after sampling by means of gas chromatography in a laboratory. These measurements are effected at comparatively large time intervals and additionally have a delay from sampling to analysis of several hours.

Indirect detection of the MCB concentration via temperature measurement at just one measurement point where there is a vapour-liquid equilibrium (VLE) is possible in principle since the components (MCB, HDI) dominate the composition of matter and all other components occur only with a small concentration or else have a higher boiling temperature than the high boilers in the binary mixture in question, such that the further components effectively do not contribute any partial pressure. A prerequisite for this procedure is a constant pressure. However, the pressure in the HDI process changes owing to different operating conditions, and so the MCB concentration cannot be run at a constant level in spite of closed-loop temperature control. Therefore, this procedure is ruled out in practice.

What is desirable for the closed-loop control of the process is a continuous determination of the MCB concentration with the sampling time of the process control system (PCS, sampling typically every second). This applies to a specific setting of an operating point (with a specification of the target value for the MCB concentration) by the plant operator, and also to rapid correction of perturbations. It is additionally desirable, using a mass balance and an energy balance over the evaporator and the ratio of the enthalpies of evaporation of the first component and the vapour stream, to calculate the temperature of the evaporator or of the separation unit. This has the advantage that it is possible to dispense with the installation of a measurement sensor.

BRIEF DESCRIPTION OF THE FIGURE

The present invention will now be described for purposes of illustration and not limitation in conjunction with the figures, wherein:

FIG. 1 shows a schematic of a plant in which the process according to the invention is conducted.

DETAILED DESCRIPTION OF THE INVENTION

The problem addressed by the present invention is that of providing a process and a system with which, in particular, the MCB concentration in the context of HDI preparation can be determined more reliably and quickly, a desired target value can be complied with and this target value can be maintained even in the presence of perturbations.

This problem is solved by a process according to claim 1 and a system according to claim 15. Advantageous developments are specified in the dependent claims. They can be combined as desired, unless the opposite is clearly apparent from the context.

A process for thermally separating a mixture comprising a first main component and a second main component, where the boiling point of the first main component is lower than the boiling point of the second main component (each under the same conditions), thus comprises the steps of:

A) evaporating a mixture of the first main component and the second main component in an evaporator by supplying thermal energy to obtain a gaseous mixture of the first main component and the second main component and a bottom product that are in a vapour-liquid equilibrium with one another;

B) transferring the gaseous mixture from step A) to a thermal separation apparatus, where the second main component at least partly condenses as bottom product in the separation apparatus, the first main component remains at least partly in the gas phase, and there is a vapour-liquid equilibrium between the bottom product and the gas phase;

C) removing the liquid bottom product from the evaporator in a first bottom product stream at a mass flow rate $F_1$;

D) removing the liquid bottom product from the separation apparatus in a second bottom product stream at a mass flow rate $F_2$;

E) combining the first and second bottom product streams to give a third bottom product stream with a mixing ratio $v=F_1/(F_1+F_2)$;

F) dividing the third bottom product stream into at least one target product stream at a mass flow rate $F_3$ and a recycle stream at a mass flow rate $F_{rec}$, where the target product stream is withdrawn and the recycle stream is recycled into the evaporator and where the target product stream has a target value for the proportions of the first and second main components.

The pressure p that exists collectively in the evaporator and/or the separation apparatus is determined therein and the temperature $T_1$ that exists in the evaporator is determined therein and the temperature $T_2$ that exists in the separation apparatus is determined therein.

p and $T_1$ are used to determine, via a first predetermined thermodynamic model, the proportions of the first and second main components in the first bottom product stream, expressed as quality $Q_1$, p and $T_2$ are used to determine, via a second predetermined thermodynamic model, the proportions of the first and second main components in the second bottom product stream, expressed as quality $Q_2$, and the qualities $Q_1$ and $Q_2$ and the mixing ratio v are used to calculate the proportions of the first and second main components in the target product stream, expressed as quality $Q_3$, as the actual value.

Finally, depending on the deviation of the actual value from the target value for the proportion of the first main component in the third bottom product stream, the supply of thermal energy to the evaporator is altered.

The first and second main components may be individual compounds. It is also possible that a multitude of compounds having similar boiling temperatures is treated as one substance and this multitude then forms the main component.

The evaporator is frequently also referred to as "reboiler". Useful thermal separation apparatuses include, but are not limited to, columns such as distillation columns or such as rectification columns, or else apparatuses for flash evaporation.

The prediction from the soft sensor can be improved by refining the thermodynamic model. In the case of known non-ideal behaviour of the mixture, the non-linearities of the liquid phase can be taken into account via the calculation of activity coefficients via a suitable $G^E$ model (excess parameter), for example an NRTL (non-random two-liquid model) approach. Non-idealities of the gas phase can be taken into account via a calculation of the coefficients of fugacity by means of a suitable equation of state (for example cubic Peng-Robinson or PC-SAFT).

In a further embodiment, therefore, the first and/or second predetermined thermodynamic model is/are selected from: a model based on the Clausius-Clapeyron equation, a model based on the Antoine equation, a non-random two-liquid model, a universal quasichemical model or a universal quasichemical functional group activity coefficients model.

In a system for thermal separation of a mixture comprising a first main component and a second main component, where the boiling point of the first main component is lower than the boiling point of the second main component (each under the same conditions), comprising a computer for control of the thermal separation, the computer is set up to control the process according to the invention.

If, for elucidation, the process and system according to the invention are elucidated in connection with the MCB concentration in the preparation process for HDI for illustration, this should not be regarded as a restriction. The solution developed is also applicable to further applications that can be described by a thermodynamic vapour-liquid equilibrium, for example two-substance or quasi-two-substance mixtures. Further possible uses can be found in the field of isocyanates inter alia.

In one embodiment, the first main component comprises a haloaromatic and/or the second main component a polyisocyanate. Examples of haloaromatics are monochlorobenzene and the isomeric dichlorobenzenes. Examples of isocyanates are 1,4-diisocyanatobutane, 1,5-diisocyanatopentane, 1,6-diisocyanatohexane (HDI), 2-methyl-1,5-diisocyanatopentane, 1,5-diisocyanato-2,2-dimethylpentane, 2,2,4- or 2,4,4-trimethyl-1,6-diisocyanatohexane, 1,10-diisocyanatodecane, 1,3- and 1,4-diisocyanatocyclohexane, 1,3- and 1,4-bis-(isocyanatomethyl)cyclohexane, 1-isocyanato-3,3,5-trimethyl-5-isocyanatomethylcyclo-hexane (isophorone diisocyanate, IPDI), 4,4'-diisocyanatodicyclohexylmethane, 4-isocyanatomethyloctane 1,8-diisocyanate (triisocyanatononane, TIN), ω,ω'-diisocyanato-1,3-dimethylcyclohexane (H6XDI), 1-isocyanato-1-methyl-3-isocyanatomethylcyclohexane, 1-isocyanato-1-methyl-4-isocyanatomethylcyclohexane, bis(isocyanatomethyl)norbornane, naphthalene 1,5-diisocyanate, 1,3- and 1,4-bis(2-isocyanato-prop-2-yl)benzene (TMXDI), 2,4- and 2,6-diisocyanatotoluene (TDI), especially the 2,4 and 2,6 isomers and technical grade mixtures of the two isomers, 2,4'- and 4,4'-diisocyanatodiphenylmethane (MDI), 1,5-diisocyanatonaphthalene, 1,3-bis(isocyanatomethyl)benzene (XDI). Preference is given to monochlorobenzene as the first main component and hexamethylene 1,6-diisocyanate (HDI) as the second main component.

The process and system according to the invention can be used to implement continuous determination of the MCB concentration with the aid of a soft sensor (the soft sensor concept includes the indirect determination of a quality-relevant parameter via simple sensors and a known physical relationship), based on a vapour-liquid equilibrium of the components and based in each case on temperature measurement and pressure measurement in the bottom of the rectification column and in the evaporator. The bottom product stream from the evaporator and the bottom product stream from the separation direction are combined. A mass balance and/or an energy balance at the mixing point can be used to ascertain the mixing ratio of the starting streams from the column bottom and evaporator and the MCB concentration of the final output stream. A further energy balance over the evaporator and the ratio of the enthalpies of evaporation of the first component to that of the vapour stream can additionally be used to calculate the bottom stream from the evaporator and hence to reconstruct a temperature in the evaporator or in the separation unit which then need not be detected by measurement. This is advantageous since a sensor constitutes an intervention into the apparatus.

The correlation between the pressure, the temperature and the molar MCB concentration for an MCB/HDI mixture which is partly evaporated and is in thermodynamic equilibrium can in principle be described via the Dalton law via the reconstruction of the pressure measured using the sum total of the partial pressures of MCB and HDI in the vapour phase. The partial pressure of the respective component in turn is proportional to the molar liquid concentration, of the vapour pressure and of the coefficient of activity. The basic relationship between the vapour pressure of a component and the temperature measured can be described via an Antoine equation. The coefficients of activity can be described, for example, via a $G^E$ model, and the coefficients of fugacity using an equation of state. With the aid of the molar masses and the calculated molar concentration, it is then possible to calculate the mass concentration of MCB in the liquid.

One advantage of the invention is that a general/generic VLE module has been developed for calculation of the physical composition for a specific process control system, which can also be applied to further physical applications. All that this requires is for the vapour pressures of the respective pure materials to be known as the Antoine equation as a function of the temperature and the molar masses, and for measurement of temperature and pressure at the point in the process in the VLE to be available or determined indirectly, for example via mass and energy balances. If the physical data are correct, no further work on interpretation or implementation is necessary.

The soft sensor concept gives a reliable, continuously available estimated value for the MCB concentration which is indicated to the plant operator in the process control system and can be used to control the process. The closed-loop control of the MCB concentration preferably replaces the closed-loop temperature control of the corresponding plant (however, the existing closed-loop temperature control system can remain as a backup in order to be activated automatically in the event of poor status of the soft sensor).

The use of the soft sensor enables running of the concentration of MCB in ranges that are novel to existing plants (for example 30% rather than 5% or 0.1% rather than 5%). Any modifications to the plant can be achieved by means of larger apparatuses (evaporator, condenser, reactor, rectification column, . . . ) with, for example, higher evaporator output or condenser output or else larger pipelines.

In the process according to the invention, detection of trends may be envisaged. If a trend for a process variable exceeds a limit (absolute value or change), an alarm can be triggered and/or the target value for the proportions of the first and second main components can be adjusted. Useful process parameters for this purpose include pressure, temperature and concentration of the first main component. The alarm can then lead to adjustment of the energy supply via the evaporator through the closed-loop control of the MCB concentration (automatically or via the plant operator) in order to counteract the perturbation which is detected by the trend. In addition, the target value for the closed-loop control can be adjusted.

If there is a fault in the plant, the soft sensor (including closed-loop control system) can compensate for this via a target value adjustment.

As shown in FIG. 1, the plant has an evaporator 100 and a thermal separation apparatus 200. In step A), a mixture comprising MCB (first main component) and HDI (second main component) is evaporated in the evaporator 100. In a further embodiment, the evaporator 100 is heated by means of steam and the steam has a mass flow rate $F_D$. Also obtained is a bottom product.

The plant has an evaporator 100 and a thermal separation apparatus 200. In step A), a mixture comprising MCB (first main component) and HDI (second main component) is evaporated in the evaporator 100. In a further embodiment, the evaporator 100 is heated by means of steam and the steam has a mass flow rate $F_D$. Also obtained is a bottom product.

In step B), as represented by stream 150, the gaseous mixture from step A) is transferred into the thermal separation apparatus 200 which may, for example, be a rectification column. The HDI as high boiler is the major component of the bottom product, and the MCB can be removed overhead. In the simplest case, the transfer is accomplished passively, i.e. via at least one pipeline that creates a fluid connection of the evaporator and the separation apparatus to one another.

In steps C), D) and E), the bottom product from the evaporator 100 in the first bottom product stream 300 is removed at a mass flow rate $F_1$ and the bottom product from the separation apparatus 200 in the second bottom product stream 400 at a mass flow rate $F_2$, and they are combined to give the third bottom product stream 500. This third bottom product stream has the mixing ratio v and the quality $Q_3$.

In step F), this third bottom product stream 500 is then divided into the target product stream 600, which is withdrawn from the process at a mass flow rate $F_3$, and a recycle stream 700 which is recycled into the evaporator 100 at a mass flow rate Free. New mixture to be separated is introduced in the feed stream to the separation apparatus 200.

In a further embodiment, the mass flow rate $F_1$ is calculated as follows:

$$F_1 = F_{Rec} - F_D \cdot (h_D / h_{K1})$$

with $h_{K1}$ as the enthalpy of evaporation of the first main component (here: MCB), $h_D$ as the enthalpy of evaporation of the steam used to heat the evaporator and $F_D$ as the mass flow rate of steam into the evaporator. $F_D$ and $F_{Rec}$ can be detected here via mass flow rate sensors.

By virtue of the fluid connection between the evaporator 100 and the separation apparatus 200, where vapour-liquid equilibria exist, the collective pressure is p, which is determined in the process according to the invention. In addition, where vapour-liquid equilibria exist, the temperature $T_1$ in the evaporator 100 and the temperature $T_2$ in the separation apparatus 200 are determined. In a further embodiment, the temperature $T_1$ is measured by means of a sensor disposed in the evaporator 100. In a further embodiment, the pressure p is measured by means of a sensor disposed in the evaporator 100. In a further embodiment, the pressure p is measured by means of a sensor disposed in the separation apparatus 200.

In the process, p and $T_1$ are used, via a first predetermined thermodynamic model, to determine the proportions of MCB and HDI in the first bottom product stream 300, expressed as quality $Q_1$.

In addition, p and $T_2$ are used, via a second predetermined thermodynamic model, to determine the proportions of MCB and HDI in the second bottom product stream 400, expressed as quality $Q_2$, and the qualities $Q_1$ and $Q_2$ are used to calculate the proportions of the first and second main components in the target product stream 600, expressed as quality $Q_3$, as the actual value. Depending on the deviation of the actual value from the target value for the proportion of the first main component in the third bottom product stream 500, the supply of thermal energy to the evaporator 100 is altered. This can be effected by means of the computer 800 and the control unit 900. The computer carries out the calculations described hereinafter. By sample measurements, it is possible to obtain the laboratory value $Q_{3,Lab}$ that can be processed by the computer as calibration parameter.

In a further embodiment, the mass flow rate $F_3$ of the target product stream 600 and the temperature $T_3$ that exists in the target product stream 600 are measured. With knowledge of the mass flow rate $F_3$, the mass flow rate $F_2$ can be calculated: $F_2 = F_3 + F_{Rec} - F_1$.

In a further embodiment, the temperature $T_2$ is calculated as follows:

$$T_2 = [c_{p,3} \cdot T_3 \cdot (F_3 + F_{Rec}) - c_{p,1} \cdot T_1 \cdot F_1]/[c_{p,2} \cdot F_2]$$

with $c_{p,1}$ as the heat capacity of the first bottom product stream 300, $c_{p,2}$ as the heat capacity of the second bottom product stream 400 and $c_{p,3}$ as the heat capacity of the target product stream 600.

In a further embodiment, the quality $Q_3$ is calculated by means of the mixing ratios v or v' as follows:

$$Q_3 = v \cdot Q_1 + (1-v) \cdot Q_2$$

or $$Q_3 = v' \cdot Q_1 + (1-v') \cdot Q_2$$

where v is as defined above and v' is calculated as follows:

$$v' = (T_3 - T_2)/(T_1 - T_2)$$

In a further embodiment, in addition, the proportions of the first and second main components in the target product stream 600 are determined experimentally at least once and the result is used to correct the calculation of the quality $Q_3$.

In a further embodiment, a correction value (pressure bias, $p_{bias}$) is added onto p. In order also to detect changes particularly in the measurement of pressure itself over time, it is additionally possible to introduce feedback of the laboratory value. Therefore, in a further embodiment, the correction value that is added onto p is calculated from the aforementioned value determined experimentally. This feedback can be expressed in the form of a correction to the pressure measurement p and reduces the discrepancy between prediction and laboratory value for the MCB concentration to a high degree.

Errors that are linear relative to pressure can thus be fully compensated for. In order to filter noise in the error feedback (caused by measurement noise in the analysis laboratory, temperature or pressure), a filter can be employed. This smooths the calculated pressure error in the case of a first-order filter (PT1) or eliminates clear outliers in the case of a median filter. Details of calculation of pressure bias can be found in equations (13), (14) later on in this text.

Alternatively or additionally to the use of pressure bias, using the laboratory or sensor data, both coefficients of activity of the partial pressures can be estimated online via an estimate on a moving horizon. Details can be found in equation (15) later on in this text. Since both coefficients of activity affect the calculation in a linear manner, the parameter estimate can be solved analytically and likewise implemented in a process control system by simple means. The adjustment of the coefficients of activity for different concentration ranges thus further reduces the prediction error of the soft sensor. Non-idealities of the gas phase can be taken into account analogously by determination of the coefficients of fugacity.

In a further embodiment, therefore, using p, $T_1$ and/or $T_2$ and the aforementioned experimentally determined value, the coefficients of activity of the partial pressures of the first main component and/or the second main component are estimated in an estimation of state based on a Kalman filter or a least-squares parameter estimate on a moving horizon.

In order to obtain a robust and reliable signal for the MCB concentration, it is advantageous to propagate the status of the temperature sensor or pressure sensor to the output of the soft sensor. In addition, it is possible in each case to define both a working range and a maximum rate of change for the temperature or pressure sensor that switch the status of the soft sensor to "poor" in the event of infringement. In a further embodiment, therefore, in addition, the operating status of sensors used is monitored and, when predetermined criteria are fulfilled, operation is switched to an alternative process. In this way, the distillation plant can be operated reliably even in the event of sensor failure. The alternative process may be the conventional laboratory-based process for determining the MCB content or else a closed-loop temperature control system.

In a further embodiment, the process is a continuous process.

Using the example of the two-substance MCB/HDI mixture, it is to be explained how the mole fraction of MCB in the liquid phase can be calculated. Raoult's law gives:

$$y_{MCB} \cdot \Phi_{MCB} \cdot p = x_{MCB} \cdot \gamma_{MCB} \cdot p_{MCB}^* \tag{1}$$

($y_{MCB}$: mole fraction of MCB in the gas phase; $\Phi_{MCB}$: coefficient of fugacity of MCB; p: total pressure; $x_{MCB}$: mole fraction of MCB in the liquid phase; $\gamma_{MCB}$: coefficient of activity of MCB; $p^*_{MCB}$: saturation vapour pressure of MCB)

The vapour pressure $p^*_{MCB}$ of the pure component depends on the temperature T (here in °C.) and can be calculated inter alia according to Antoine with the parameters A, B and C:

$$p^*_{MCB} = \exp(A_{MCB} + B_{MCB}/(C_{MCB} + 273.15 + T)) \tag{1b}$$

Equation (1) rearranged for p gives:

$$p = \frac{x_{MCB} \cdot \gamma_{MCB} \cdot p^*_{MCB}}{y_{MCB} \cdot \Phi_{MCB}} \tag{2}$$

The pressure p is the sum total of the partial pressures:

$$p = p_{MCB} + p_{HDI} \tag{3}$$

($p_{MCB}$: partial pressure of MCB in the gas phase; $p_{HDI}$: partial pressure of HDI in the vapour phase)

The partial pressures can be formulated for ideal coefficients of fugacity $\Phi_{MCB}$ and $\Phi_{HDI}$ as follows:

$$p_{MCB} = x_{MCB} \cdot \gamma_{MCB} \cdot p_{MCB}^* \tag{4}$$

$$p_{HDI} = x_{HDI} \cdot \gamma_{HDI} \cdot p_{HDI}^* \tag{5}$$

In the two-substance mixture, $x_{MCB}+x_{HDI}=1$ can be defined. Then the partial HDI pressure can be formulated as follows ($p_{HDI}^*$: saturation vapour pressure of HDI):

$$p_{HDI}=(1-x_{MCB})\cdot\gamma_{HDI}\cdot p_{HDI}^* \quad (6)$$

When the expressions for the partial pressures are inserted into equation (3), this gives:

$$p=(x_{MCB}\cdot\gamma_{MCB}\cdot p_{MCB}^*)+((1-x_{MCB})\cdot\gamma_{HDI}\cdot p_{HDI}^*) \quad (7)$$

$$p=(x_{MCB}\cdot\gamma_{MCB}\cdot p_{MCB}^*)+((\gamma_{HDI}-x_{MCB}\cdot\gamma_{HDI})\cdot p_{HDI}^*) \quad (8)$$

$$p=(x_{MCB}\cdot\gamma_{MCB}\cdot p_{MCB}^*)+(\gamma_{HDI}\cdot p_{HDI}^*-x_{MCB}\cdot\gamma_{HDI}\cdot p_{HDI}^*) \quad (9)$$

Solving for $x_{MCB}$ gives:

$$p-\gamma_{HDI}\cdot p_{HDI}^* = x_{MCB}\cdot\gamma_{MCB}\cdot p_{MCB}^* - x_{MCB}\cdot\gamma_{HDI}\cdot p_{HDI}^* \quad (10)$$

$$p-\gamma_{HDI}\cdot p_{HDI}^* = x_{MCB}\cdot(\gamma_{MCB}\cdot p_{MCB}^* - \gamma_{HDI}\cdot p_{HDI}^*) \quad (11)$$

$$\frac{p-\gamma_{HDI}\cdot p_{HDI}^*}{\gamma_{MCB}\cdot p_{MCB}^* - \gamma_{HDI}\cdot p_{HDI}^*} = x_{MCB} \quad (12)$$

On the left-hand side of the equation are solely terms that can be measured, can be calculated from the temperature or can be obtained/simulated from databases.

With the molar masses $MW_{MCB}$ and $MW_{HDI}$, the mass concentration $x_{mass,MCB}$ is obtained:

$$x_{mass,MCB} = \frac{x_{MCB}\cdot MW_{HDI}}{x_{MCB}\cdot MW_{HDI} + x_{HDI}\cdot MW_{HDI}} \quad (12b)$$

The calculation of the correction value for the pressure $p_{bias}$ is found from the deviation between one calculated pressure value $p_{calc}$ which corresponds to the laboratory analysis $x_{MCB}$ and the pressure p measured by the sensor:

$$p_{calc,i}=(x_{MCB,labor,i}\cdot\gamma_{MCB,i}\cdot p_{MCB,i}^*)+(\gamma_{HDI,i}\cdot p_{HDI,i}^* - x_{MCB,labor,i}\cdot\gamma_{HDI,i}\cdot p_{HDI,i}) \quad (13)$$

$p_{bias}$ is calculated as the median of the differences $p_{calc,i}$ and $p_{sensor,i}$ ($p_{sensor}$ denotes the pressure measured by the sensor, i denotes the index of the laboratory sample) across a horizon of length n+1, where k denotes the last laboratory sample analysed:

$$p_{bias}=\text{median}(p_{calc,k}-p_{sensor,k},p_{calc,k-1}-p_{sensor,k-1},\ldots,p_{calc,k-n}-p_{sensor,k-n}) \quad (14)$$

Thus, the measured value $p_{sensor}$ can be corrected with $p_{bias}$ as input value for the pressure p in equation (12):

$$p=p_{sensor}+p_{bias} \quad (14b)$$

As an alternative to the median filter, the correction value for the pressure $p_{bias}$ can also be calculated via a first-order (PT1) or higher-order filter. One way of implementing a PT1 filter in a time-discrete manner is as follows, with $\Delta t$ as sampling time for the sampling for the laboratory analysis and $T_{Filter}$ as filter time:

$$p_{bias,k} = \frac{\Delta t}{T_{filter}+\Delta t}*(p_{calc,k}-p_{sensor,k})+\frac{T_{filter}}{T_{filter}+\Delta t}*p_{bias,k-1}, \quad (14c)$$

where $p_{bias,k}$ is the current correction value and $p_{bias,k-1}$ the previous correction value. In a further embodiment, parameters in the calculation can be fitted to the data obtained in the course of production. One way of doing this is to estimate the coefficients of activity $\gamma_{MCB}$ and $\gamma_{HDI}$ via a least-squares method in order to fit the prediction of the above-described process to the laboratory data $x_{MCB,lab,i}$, based on data across a horizon of length n+1, where index k denotes the last laboratory sample analysed:

$$\min_{\gamma_{MCB},\gamma_{HDI}} \sum_{i=k-n}^{k} (x_{MCB,lab,i}-x_{MCB,calc,i})^2 \quad (15)$$

under condition of (1)-(13)

The estimated coefficients of activity can be varied as a function of temperature and physical composition for non-ideal behaviour of the liquid-vapour mixture. By this procedure, it is thus possible to detect the non-ideal behaviour of the mixture depending on the conditions (temperature, pressure).

The correction value or coefficients of activity are calculated as soon as a new laboratory sample has been evaluated, i.e. with the sampling time of the sampling. The length of the horizon or filter time $T_{filter}$ typically corresponds to 10-50 samplings.

The invention claimed is:

1. A process for thermally separating a mixture comprising a first main component and a second main component, where the boiling point of the first main component is lower than the boiling point of the second main component, the process comprising:

A) evaporating a mixture of the first main component and the second main component in an evaporator by supplying thermal energy to obtain a gaseous mixture of the first main component and the second main component and a first bottom product that are in a vapor-liquid equilibrium with one another;

B) transferring the gaseous mixture from A) to a thermal separation apparatus, where the second main component at least partly condenses as a second bottom product in the separation apparatus, the first main component remains at least partly in a gas phase, and there is a vapor-liquid equilibrium between the second bottom product and the gas phase;

C) removing the first bottom product from the evaporator in a first bottom product stream at a mass flow rate $F_1$, wherein the first bottom product stream is removed from the evaporator separately from the gaseous mixture;

D) removing the second bottom product from the separation apparatus in a second bottom product stream at a mass flow rate $F_2$;

E) combining the first and second bottom product streams to give a third bottom product stream with a mixing ratio $v=F_1/(F_1+F_2)$, in which $F_1$ is a mass flow rate for removing the first bottom product stream and $F_2$ is a mass flow rate for removing the second bottom product stream;

F) dividing the third bottom product stream into at least one target product stream at a mass flow rate $F_3$ and a recycle stream at a mass flow rate $F_{rec}$, where the target product stream is withdrawn and the recycle stream is recycled into the evaporator and where the target product stream has a target value for the proportions of the first and second main components;

the process further including determining the pressure p that exists collectively in the evaporator and/or the separation apparatus, determining the temperature $T_1$ that exists in the evaporator, determining the temperature $T_2$ that exists in the separation apparatus, determining according to a first predetermined thermodynamic model, from p and $T_1$ which are the proportions of the first and second main components in the first bottom product stream, expressed as quality $Q_1$, determining according to a second predetermined thermodynamic model, p and $T_2$ which are the proportions of the first and second main components in the second bottom product stream, expressed as quality $Q_2$, calculating based on the qualities $Q_1$ and $Q_2$ and the mixing ratio v, the proportions of the first and second main components in the target product stream, expressed as quality $Q_3$, as the actual value and, altering the supply of thermal energy to the evaporator depending on the deviation of the actual value from the target value for the proportion of the first main component in the third bottom product stream.

2. The process according to claim 1, wherein the first main component is a haloaromatic and/or the second main component comprises a polyisocyanate.

3. The process according to claim 1, wherein the evaporator is heated by steam having a mass flow rate $F_D$.

4. The process according to claim 3, wherein the mass flow rate $F_1$ is calculated as follows:

$$F_1 = F_{Rec} - F_D \cdot (h_D / h_{K1})$$

wherein $h_{K1}$ is enthalpy of evaporation of the first main component, $h_D$ is enthalpy of evaporation of the steam heating the evaporator, and $F_D$ is the mass flow rate of steam into the evaporator.

5. The process according to claim 1, wherein the temperature $T_1$ is measured by a sensor disposed in the evaporator and/or wherein the pressure p is measured by a sensor disposed in the evaporator.

6. The process according to claim 1, further including measuring the mass flow rate $F_3$ of the target product stream and the temperature $T_3$ in the target product stream.

7. The process according to claim 6, wherein the mass flow rate $F_2$ is calculated as follows:

$$F_2 = F_3 + F_{Rec} - F_1.$$

8. The process according to claim 7, wherein the temperature $T_2$ is calculated as follows:

$$T_2 = [c_{p,3} \cdot T_3 \cdot (F_3 + F_{Rec}) - c_{p,1} \cdot T_1 \cdot F_1] / [c_{p,2} \cdot F_2]$$

wherein $c_{p,1}$ is heat capacity of the first bottom product stream, $c_{p,2}$ is heat capacity of the second bottom product stream and $c_{p,3}$ is heat capacity of a target product stream.

9. The process according to claim 8, wherein quality $Q_3$ is calculated by a mixing ratio v or v' as follows:

$$Q_3 = v \cdot Q_1 + (1-v) \cdot Q_2$$

or $$Q_3 = v' \cdot Q_1 + (1-v') \cdot Q_2$$

wherein v' is calculated as follows:

$$v' = (T_3 - T_2)/(T_1 - T_2).$$

10. The process according to claim 1, further including determining the proportions of the first and second main components in the target product stream experimentally at least once and correcting the calculation of the quality $Q_3$ with the experimentally determined proportions.

11. The process according to claim 1, wherein a correction value is added onto p.

12. The process according to claim 11, wherein the correction value added onto p is calculated from a value determined experimentally.

13. The process according to claim 10, further including estimating coefficients of activity of the partial pressures of the first main component and/or the second main component with p, $T_1$ and/or $T_2$ and the value determined experimentally, =in an estimation of state based on a Kalman filter or a least-squares parameter estimate on a moving horizon.

14. The process according to claim 1, further including monitoring operating status of sensors and, switching operation to an alternative process when predetermined criteria are fulfilled.

* * * * *